United States Patent

Wagner

[11] Patent Number: 5,277,876
[45] Date of Patent: Jan. 11, 1994

[54] VALVE APPARATUS AND METHOD FOR STERILIZER CONTAINER

[75] Inventor: Peter Wagner, Starnberg, Fed. Rep. of Germany

[73] Assignee: Wagner GmbH Fabrik Fur Medizinische, Fed. Rep. of Germany

[21] Appl. No.: 973,610

[22] Filed: Nov. 6, 1992

Related U.S. Application Data

[63] Continuation of Ser. No. 466,347, filed as PCT/EP89/00703, Aug. 3, 1988, abandoned.

[30] Foreign Application Priority Data

Aug. 28, 1987 [DE] Fed. Rep. of Germany ........ 8711702
Aug. 28, 1987 [DE] Fed. Rep. of Germany ........ 8711703
Jun. 29, 1988 [DE] Fed. Rep. of Germany ........ 8808353

[51] Int. Cl.$^5$ ............................................. G05D 7/00
[52] U.S. Cl. .................................... 422/110; 137/72; 422/103; 422/112
[58] Field of Search ............... 422/110, 103, 112, 113, 422/296; 137/67, 72

[56] References Cited

U.S. PATENT DOCUMENTS

| | | | |
|---|---|---|---|
| 4,196,166 | 4/1980 | Sanderson et al. | 422/33 |
| 4,228,914 | 10/1980 | Sanderson | 422/112 |
| 4,251,482 | 2/1981 | Jenkins | 422/26 |
| 4,349,118 | 9/1982 | Sanderson et al. | 220/201 |
| 4,457,327 | 7/1984 | Pepper | 137/67 |
| 4,729,876 | 3/1988 | Hennessy et al. | 422/103 |
| 4,748,003 | 5/1988 | Riley | 422/103 |

FOREIGN PATENT DOCUMENTS

2335239 10/1976 France.

Primary Examiner—Robert J. Warden
Assistant Examiner—Laura E. Collins
Attorney, Agent, or Firm—Osterlenk, Faber, Gerb & Soffen

[57] ABSTRACT

A valve for a sterilizer container comprises an elastic support body in the form of a pressure capsule which holds the valve in open position. This pressure capsule communicates with the interior of a headpiece which is sealingly arranged on the valve cap, the capsule having a valve opening which can be closed by the plug of an adjusting member. The closing is effected, after the sterilization temperature has been reached, by a temperature-sensitive member which has an alloy which melts when the sterilization temperature is reached. The alloy when in solidified state holds the adjusting member, which is under spring tension, fast and permits it to move as soon as it melts. The adjusting member can be clamped by means of a one-way coupling when the alloy is solidified. The entire valve arrangement can be removed from the container. It preferably lies in a cup-shaped depression in the lid of the container, the possibility of stacking with other containers being thus assured.

10 Claims, 6 Drawing Sheets

VALVE APPARATUS AND METHOD FOR STERILIZER CONTAINER

This is a continuation of application Ser. No. 07/466,347, filed as PCT/EP89/00703, Aug. 3, 1988.

BACKGROUND OF THE INVENTION

The present invention relates to a method of controlling a valve for a sterilizer container and a valve suitable for carrying out the method. Such valves make possible an exchange of fluid into and out of the sterilizer container within a sterilizer. The valve body of this valve is closed during the last vacuum phase while maintaining a vacuum in the container controlled via a pressure sensor and a temperature member.

Such valves are known, for instance, from U.S. Pat. No. 4,251,482 and U.S. Pat. No. 4,228,914. As compared with known double check-valve arrangements of other sterilizer containers they have the advantage that the interior of the sterilizer container is in free communication, until entrance into the vacuum of the drying phase, with the interior of the sterilizer chamber so that a fluid exchange can continuously take place. The valves controlled as a function of the pressure and temperature furthermore have the advantage that after the end of the sterilization process the vacuum remains within the container.

U.S. Pat. No. 4,251,482/U.S. Pat. No. 4,228,914 show sterilizer containers having a valve, arranged in their bottoms, which is closed by a bellows-like expansion chamber. A shrinkable tube closes an opening which leads to the inside of the bellows and, upon a drop in the external pressure, the bellows expands and closes the valve. The thermal shrinkage of the tube takes place during the sterilization phase at a point in time which is not precisely defined. The closing of the valve takes place also in a manner not precisely defined in time still prior to the vacuum-drying -drying phase. The steam is not to be withdrawn through the valve but through the container lid above the seal, i.e. the lid must not close tightly during the vacuum-drying phase so that steam and moisture can be led away.

In the arrangement described in U.S. Pat. No. 4,251,482 there is provided as the pressure sensor an expansion vessel which is thermally closed in the steam sterilization phase by a shrink tube which thus blocks an inlet opening of the expansion vessel. This has the result that the pressure sensor upon introduction into the after-drying vacuum phase expands under the action of the pressure present in it. This expansion is used to displace a valve body into closed position, as a result of which the sterilizer container is sealed off. In the last vacuum phase, i.e. during the drying phase, the valve remains closed and can no longer contribute to the fluid exchange.

A drawing off of the steam phases produced by re-evaporation of the condensate must therefore take place through the container-lid seal or it is necessary to provide in addition, as described in U.S. Pat. No. 4,228,914, an additional valve which opens when a vacuum is applied to the outside of the container in order in this way to be able to withdraw the steam.

In the sterilizer container of French-A No. 2,335,239 there is again provided in the bottom a valve which in this case is brought into closed position not by a shrinkable tube but by a melting eutectic. It is completely impossible in this connection for the closing of the valve to take place in the ventilation phase since the eutectic melts during the sterilization phase B and, upon the melting, the valve is immediately brought into the closed position. The drying can in this case also again take place only via the lid seal during the vacuum-drying phase. However, the valve body is not controlled into the closing position only upon the ventilation phase. To this extent the manner of operation of the valve of the invention differs fundamentally from that of the known valve.

SUMMARY OF THE INVENTION

The object of the invention is to provide a valve control method and a valve for a sterilizer container which is open not only in the pre-vacuum phase and the sterilization phase but also still during the final after-drying vacuum phase and which closes only after introduction of the ventilation phase.

The essence of the present invention by which it differs fundamentally from the known prior art consists in the fact that with the valve, the container is closed during the ventilation phase. In this way, assurance is had that the entire vacuum phase is available for the drying, since moisture can still escape up into the ventilation phase.

In accordance with the invention, the closing of the valve takes place by the squeezing together of the pressure sensor which keeps the valve open, after commencement of the ventilation phase as a result of the increasing external pressure against which the pressure capsule which forms the pressure sensor is blocked off, controlled by the temperature member. The thermal control is effected by the steam-sterilization temperature, but is not decisive for the action in accordance with the invention when, specifically during the sterilization phase, the temperature member effects the closing of the pressure sensor. It is merely necessary that it closes the pressure sensor before the last pressure increase has been reached (ventilation phase).

This can, for instance, take place in the manner that an alloy or other material which melts at the specific sterilization temperature used, holds the pressure sensor valve in open position until this temperature is reached.

The pressure sensor has a check valve which permits a ventilating of the pressure sensor upon a drop in the outside pressure but closes it again upon an increase in pressure so that a vacuum which has once been applied is maintained in the pressure sensor.

In contradistinction to known valve arrangements, no temperature control of the container valve is effected, the temperature control effecting merely the preparation of the pressure sensor of the valve closing process during the ventilation phase. By adjustment of a tensioning spring which keeps the container valve in open position, the amount of the vacuum at which the valve closes can be precisely established.

The valve of the invention can be arranged on the container or on the container lid, it being advisedly connected in detachable manner therewith so that it can be cleaned separately and possibly replaced by another one the alloy of which has a different melting point which is adapted to a different sterilization temperature.

Summarizing, the following advantages result from the valve of the invention as compared with comparable valves:

The container valve which permits the exchange of fluids remains open during the entire sterilization cycle up to the increase in pressure upon the ventilation.

Therefore, it is not closed, as in the case of the known prior art, already upon entrance into the drying phase but remains open so that an optimum drawing off of the condensate which again vaporized in the vacuum phase from the container is assured without being impeded by flow resistances such as filters or applied seals.

The closing of the valve takes place at a predeterminable vacuum. The amount of the enclosed vacuum can be easily adjusted via the ratio of effective cross-sections and spring forces. The vacuum remaining in the container can, in contradistinction to known arrangements, accordingly be set less than the vacuum of the drying phase, which amounts to about 100 mbar. Accordingly, the pressure difference which acts on the container after the conclusion of the ventilation is correspondingly less than in the case of the prior art, in which correspondingly pressure-resistant special constructions which are unusual in practice are required.

Furthermore, by the valve of the invention, the penetration of air or gases, and thus also of bacteria, during transportation and storage is reliably prevented. The closing of the valve takes place, for instance, at a chamber pressure of 800 mbar which prevails, in fact, at this time also in the sterilizer container and the rest of the pressure increase to 1000 mbar then takes place, but it, however, can no longer be compensated for by the container due to the closed valve, so that the entire valve cap is pressed from the outside by the pressure difference of 200 mbar and thus is sealed.

In order to limit the vacuum it would, theoretically to be sure, also be possible to use a spring-loaded check flap or a check valve in the container with fixed response pressure of, for instance, 200 mbar. Upon ventilation via such a valve to 1000 mbar outside pressure, 800 mbar vacuum would then also be established in the container. However, upon removal from the sterilizer there is then the danger of contamination unless the penetration of bacteria into the container is dependably avoided by suitable designs of the flow path.

At the end of the ventilation, the system is then in equilibrium, i.e. the pressure difference present of 200 mbar would then just be insufficient to open the check flap against the spring force. However, if the outside pressure increases, for instance due to barometric variations, during storage (up to 60 mbar) or if the inside pressure decreases by the cooling of the approximately 80° C. sterilizer container, then the check flap would open briefly for pressure equalization and there would be the danger of contamination of the sterile content, although any possibly still present but reduced residual vacuum would falsely suggest to the user that the container was air-tight. This danger is excluded when using the valve of the invention since the valve is closed only in the final ventilation phase at an adjustable vacuum and then remains sealed by the atmospheric pressure acting from the outside on the container until opening. The indication of the vacuum indicator or the whistling upon the opening of the container as a result of the incoming air is a dependable indication that the container was gas-tight from its sterilization until its opening and thus free of bacteria.

Other features and advantages of the present invention will become apparent from the following description of the invention which refers to the accompanying drawings.

BRIEF DESCRIPTION OF THE DRAWINGS

Several embodiments of the invention will be described below with reference to the accompanying drawings, in which.

DETAILED DESCRIPTION

The lid 10 of the sterilizer container has, in its center, a cup-shaped depression 12 the bottom 14 of which is provided with fluid-exchange openings 16. Within the cup-shaped depression 12 there is a valve cap 18, the sealing ring 20 of which seals against the bottom 14 of the depression in the closed position of the valve. The fluid-exchange openings 16 are located radially within the area of the bottom 14 enclosed by the sealing ring 20. Between the cap or the seal 20 and the side wall 22 of the cup-shaped depression there is a cylindrical annular gap 24 which is sufficiently wide to assure the free exchange of fluid when the valve is open.

The cover plate of the valve cap 18 bears concentrically on its inside a pot-shaped support body 26, the outer flange 28 of which is clamped in sealing manner against the valve cap by means of a clamping rim 30 on the cap. The support body 26 consists of a resilient material and is axially compressible as a function of pressure differences. The support body 26 may comprise, e.g., a folded bellows or a spring loaded membrane. On the bottom of the support body, there rests a washer 32, in the internal thread of which a screw 34 is screwed, the screw being inserted from below through a hole in the bottom part of the pot-shaped support body 26. The screw 34 is connected in sealed manner, for instance by bonding, to the bottom part. Over the screw 34 there is placed a coil spring 36 which, in installed condition, rests on the one side against the bottom of the pot-shaped support body 26 and on the other side against the bottom 14 of the cup-shaped depression. This bottom has a central X-shaped slot 38 through which a correspondingly X-shaped screwhead 40 of the screw 34 is inserted from above and fastened by turning. Within the pot-shaped support body 26 there is a compression coil spring 42 which rests against the washer 32 and the cover of the cap 18 and axially extends the support body 26 so that this support body, when there is no pressure difference, assumes the position shown in FIG. 3 in which it lifts the valve cap and its sealing ring 20 from the bottom 14 and thereby holds the valve open. The valve closes when, at a predetermined pressure difference, the support body 26 is squeezed axially together against the force of the spring 42. The spring 4 thus acts as a biasing means.

This function will be described in detail further below.

Figure 1:
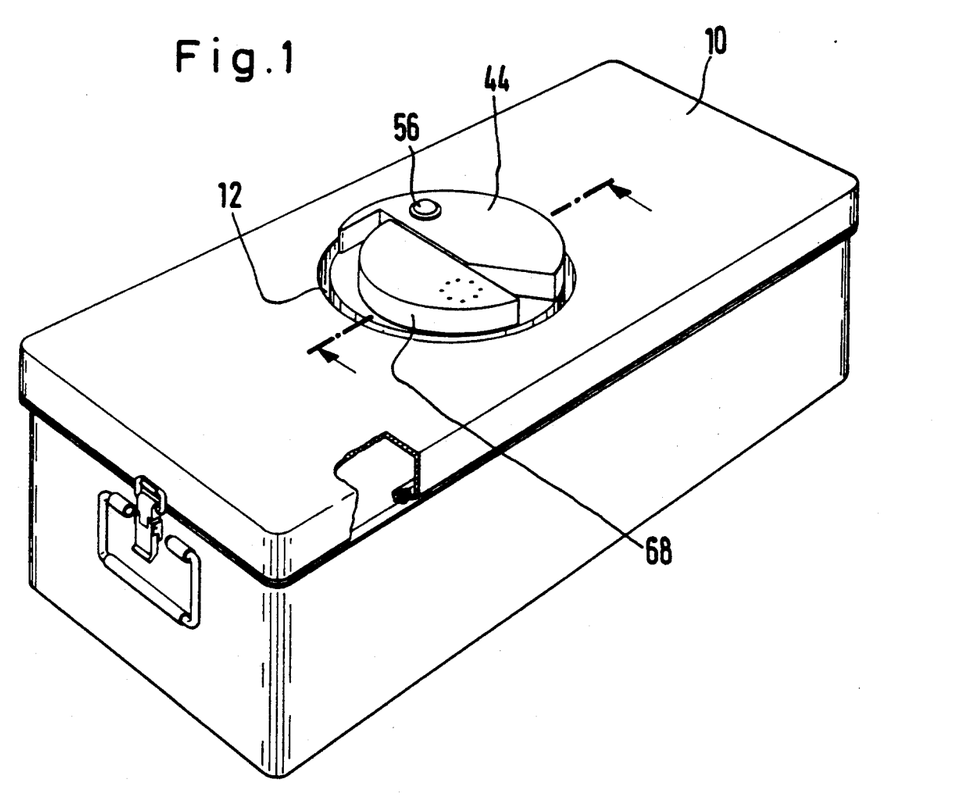
FIG. 1 is perspective view of a sterilizer container having a valve in a lid in accordance with the invention.
Figure 2:
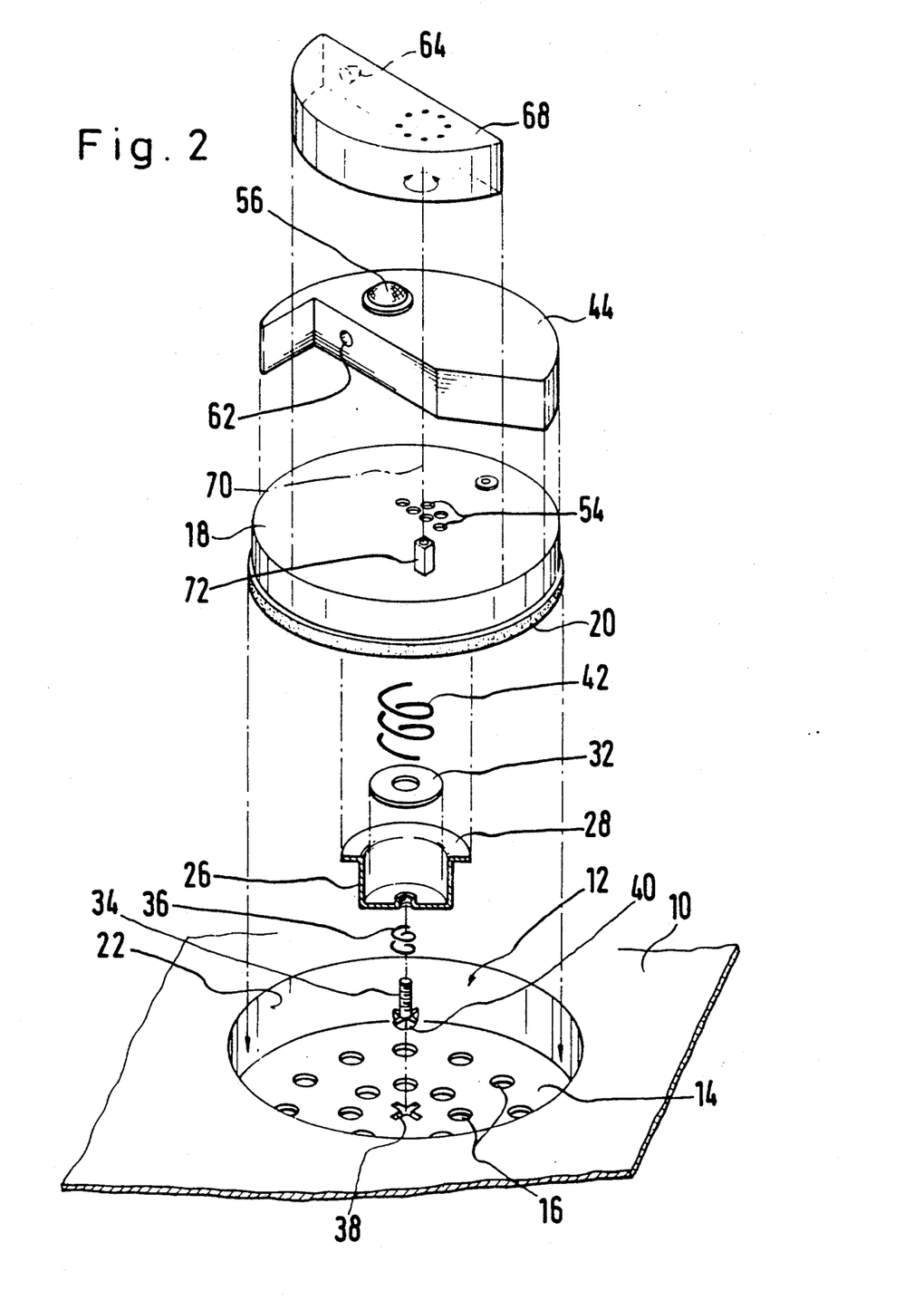
FIG. 2 is an exploded perspective view of the valve.
Figure 3:
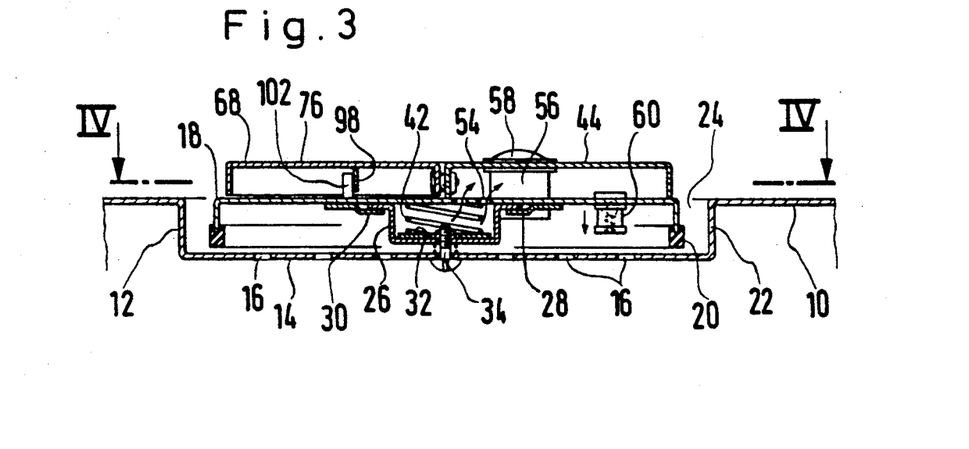
FIG. 3 is a section along the line III—III of FIG. 1 or FIG. 4.

The valve cap 18 bears a hollow headpiece 44, the shape of which can best be noted from FIG. 2. In accordance with the embodiment shown, the side wall of the headpiece 44 has a circular-cylindrical section 46 extending over about 180° and a section 48 extending over a part of a diameter as well as two chordal sections 50 and 52. The first chordal section 50 extends, as can be noted from FIG. 4, at a right angle to the diameter section 48 and connects the latter to the annular wall 46. The second chordal section 52 is set back, as can be noted in FIG. 4, with respect to the diameter section 48 and forms an obtuse angle with the latter. This headpiece 44 is placed in vacuum-tight manner on the valve cap 18 or is developed in one piece with it. Passage holes 54 in the valve-cap cover plate connect the inside of the headpiece 44 with the inside of the pot-shaped support body 26. The cover plate of the headpiece 44 bears a vacuum indicator 56. The latter has a sealingly clamped membrane 58 which is arched outward (as shown in FIGS. 2 and 3) by an inner spring (not shown) and which is pulled inward as soon as the interior is under a pressure less than the outside pressure.

In the region of the headpiece 44 a one-way check valve 60 is inserted in the cover of the valve cap 18, it permitting, for reasons which will be explained further below, flow from the inside of the headpiece 44 to the outside but not in the opposite direction.

Figure 5:
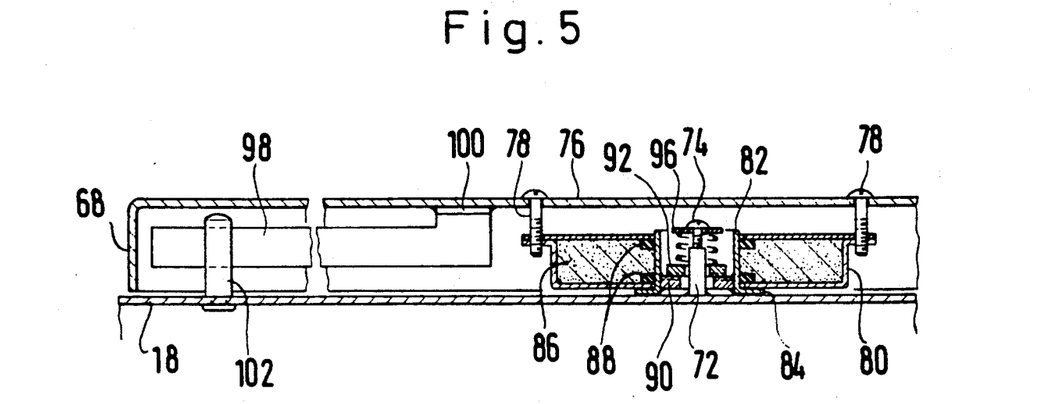
FIG. 5 shows a section on a larger scale along the line V—V of FIG. 4.
Figure 6:
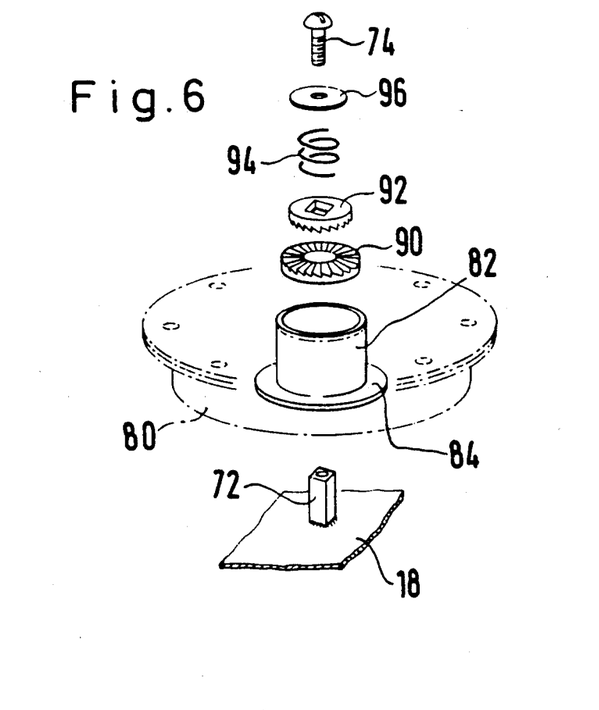
FIG. 6 is an exploded perspective view of the switch device for the valve.

The wall section 48 has a valve opening 62 comprising part of an auxiliary valve which can be closed by a plug 64. This plug 64 protrudes from the side wall 66 of a semi-cylindrical adjusting member 68 which is swingable, around an axis 70 which is eccentric with respect to the cylinder axis of the valve cap 18, between the closed position shown in solid line in FIG. 4 and the open position shown in dash-dot line. As can be noted from FIG. 4, the adjusting member 68 is located in its open position, indicated by dash-dot line, in part outside of the cup-shaped depression 12 and above the plane of the container lid so that the closing of the valve cap is prevented in this position. The adjusting member is held in this open position in a manner which will be described below until it is brought, controlled by the temperature, into the closed position. The manner of operation and the switching device for the adjusting member 68 can best be noted from FIGS. 5 and 6.

A pin 72 of polygonal cross section is welded or otherwise fastened on the top of the cover of the valve cap 18. The pin has a threaded bore lying in its axis 70, into which bore a screw 74 can be screwed. The cover plate 76 of the adjusting member 68 is connected by screws 78 to a drum 80. This drum 80 surrounds a sleeve 82 which lies concentric to the axis 70 and rests with its outer flange 84 on the valve cap 18. The drum 80, which is open in the direction of the sleeve 82, is filled with a composition 86 of preferably a eutectic metal alloy which melts upon reaching a predetermined sterilization temperature, for example 121° C. or 134° C.

In solidified state, the eutectic 86 adheres to the drum 80 and to the sleeve 82 or is shrunk onto the sleeve so that, in this state, the drum 80 or adjusting member 68 and sleeve 82 are connected together in a manner fixed against rotation. If necessary, the sleeve 82 can have outwardly pointing projections in the form of pins, screws, bumps or the like which assure a form-locked attachment. As soon as the eutectic 86 has been heated to the sterilization temperature of, for instance, 121° C. or 134° C., it melts and the rotationally fixed connection between drum 80 and sleeve 82 is done away with. Flowing of the eutectic out of the drum 80 is prevented by packing rings 88.

Within the sleeve 82 there is fastened a toothed disk 90 with axial toothing which surrounds the pin 72 with clearance and is freely rotatable with respect to the latter. Another toothed disk 92 lies against the toothed disk 90 in such a manner that their toothings engage axially in each other. The toothings of the toothed disks 90 and 92 are so developed as saw teeth that a slip coupling is produced, as will be described further below. The toothed disk 92 has a polygonal hole which corresponds to the cross-section of the pin 72 and it is placed fixed against rotation on the pin 72. The toothed disks 90 and 92 are pressed against each other by a compression coil spring 94 which is placed over the screw 74 and which rests at one end against the toothed disk 92 and at the other end against a washer 96 which rests against the head of the screw 74.

The adjusting member 68 is urged into the closed position by a leaf spring 98. This leaf spring 98 is fixed at one end 100 to the cover plate 76 of the adjusting member 68 and extends outward parallel to the cover plate. The free end of the leaf spring 98 lies against a pin 102 which protrudes upward from the valve cap 18.

Figure 4:
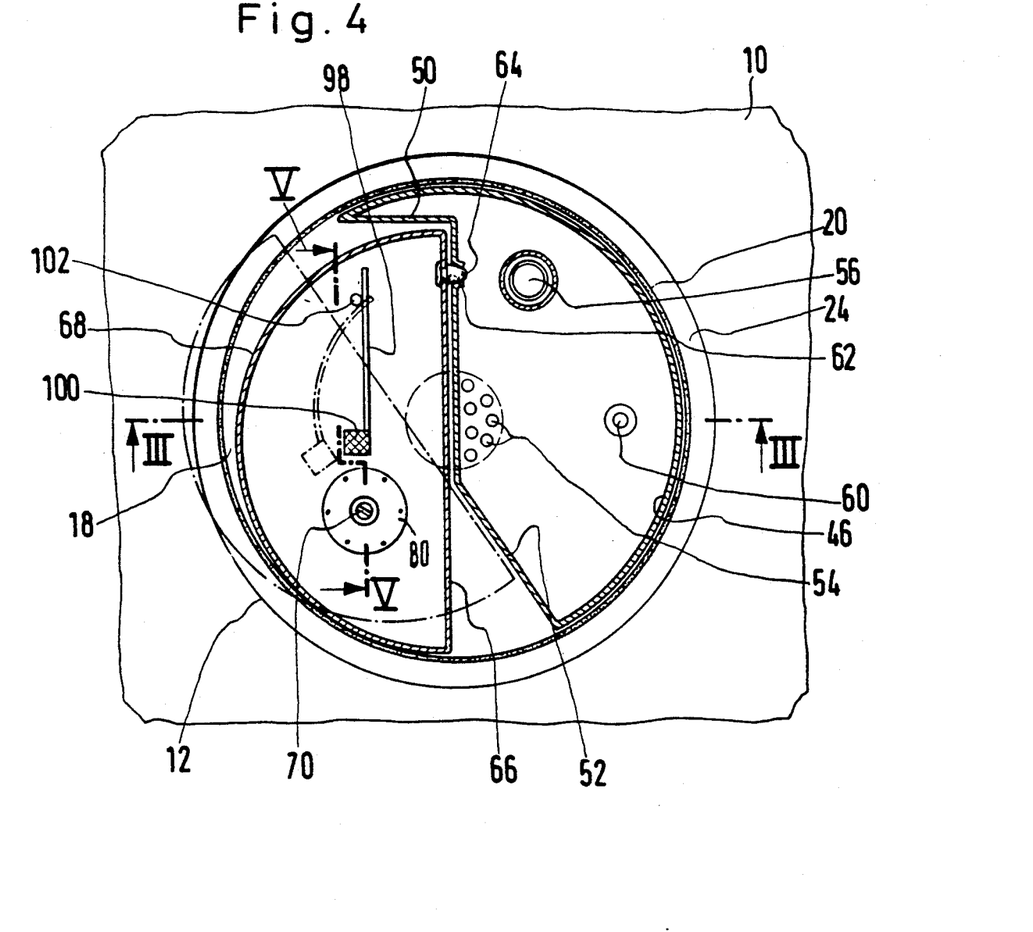
FIG. 4 is a section along the line IV—IV of FIG. 3.

With the eutectic 86 solidified, the adjusting member 68 can be moved by hand from the closed position shown in solid line in FIG. 4 into the open position shown in dash-dot line in FIG. 4, the spring 98 being thereby cocked. In this position, a closing movement of the valve is mechanically blocked, as can be noted from FIG. 4, so that the valve 18 cannot be closed by the dynamic pressure of the incoming steam. The mechanical blocking can be produced in the manner that the turnable adjustment member swings above the side wall 22 over the edge of the cover and is held fast there. Upon the cocking of the adjusting member, the sleeve 82 is turned in counterclockwise direction as shown in FIG. 4 via drum 80 which is firmly connected to it, the toothings of the toothed disks 90 and 92 being able to slip on each other. In the opposite direction, i.e. in clockwise direction in FIG. 4, a connection fixed against rotation is produced via the toothings so that the adjusting member is held in the open position since the toothed disk 92 is seated fixed against rotation on the pin 72 which is fixed on the valve cap 18. In accordance with the embodiment shown, the valve protrudes over the surface of the container lid. In order that the containers can be stacked, they must either have feet of suitable length or the valve must be arranged in another stepped depression below the surface of the lid.

The valve of the invention operates as follows:

The entire valve mechanism, contained in the cuplike depression 12 in the lid of the sterilizer container, can be connected to the latter in easily detachable fashion. It can be cleaned as a separate unit. In clean condition it is connected to the sterilizer container in the manner that the X-shaped screw head 40 is inserted into the X-shaped slot 38 of the bottom 14 and the entire valve unit is turned up against a stop, as a result of which the screw head is locked in bayonet-like fashion. After the insertion, the valve remains open, i.e., the sealing ring 20 remains at a distance from the bottom 14. In this condition, the sterilizer container is brought into the sterilizer and evacuated several times in the initial phase A (see FIG. 7). An increase in temperature then takes place up to a maximum value which, depending on the nature of the material to be sterilized is, for instance, 121° C. or 134° C. The adjustment to the proper sterilization temperature can be effected by replacement of the valve arrangement. For different sterilization temperatures a different alloy 86 which melts at this temperature is used.

During the pre-vacuum phase A, the eutectic 86 remains solid and the adjusting member 68 remains in the position shown in dash-dot line in FIG. 4. Thus the auxiliary valve comprising opening 62 and plug 64 remains open and a sensor sterilizing-chamber pressure equalization can continuously take place so that the pressure required for the closing of the valve cap 18 cannot build up.

In the first section B1 of the sterilizing phase B, the eutectic 86 melts and, as a result, the frictional connection or form-locked connection between the eutectic 86 and the sleeve 82 is done away with. In this way, the pretensioned adjusting member is moved from the open position shown in dash-dot line in FIG. 4 by the spring 98 into the closed position shown in solid line in FIG. 4, in which position the plug 64 closes the valve opening 62. In this way, the interior of the headpiece 44 together with the interior of the pot-shaped support body is closed off from the outer atmosphere. Via the check valve 60, the flow can now take place only outward from the chamber formed by the headpiece 44. The check valve 60 can have a replaceable filter element.

After the end of the sterilizing phase B the outside pressure decreases in a first section C1 of the drying phase C and evacuation of the pressure sensor comprising the headpiece 44 and support body 16 to approximately chamber pressure takes place via the check valve 60. The valve cap 18, however, is still in open position. During the ventilation phase D the valve cap is brought into the closed position due to the fact that the outside pressure rises again but pressure equalization via the check valve cannot take place, so that a lower pressure remains within the chamber 44 and within the support body 26 and the support body collapses and the bottom 14 comes to lie in sealing fashion against the valve cap 18. The support body 16 and the hollow headpiece 44 thus operate as a pressure sensor or pressure-sensitive member. In contradistinction to other valve arrangements, the valve of the invention operates properly even if moist air is repeatedly drawn out of the container in a fractionated after-drying phase CF and replaced by dry air, i.e. when pressure changes take place in the drying phase. Then a repeated opening and closing takes place and the valve is in this case closed by the last ventilation phase DL at a predetermined pressure difference. This fractionated after-drying phase is indicated in FIG. 7 to the right of the dash-dot line L.

Figure 7:
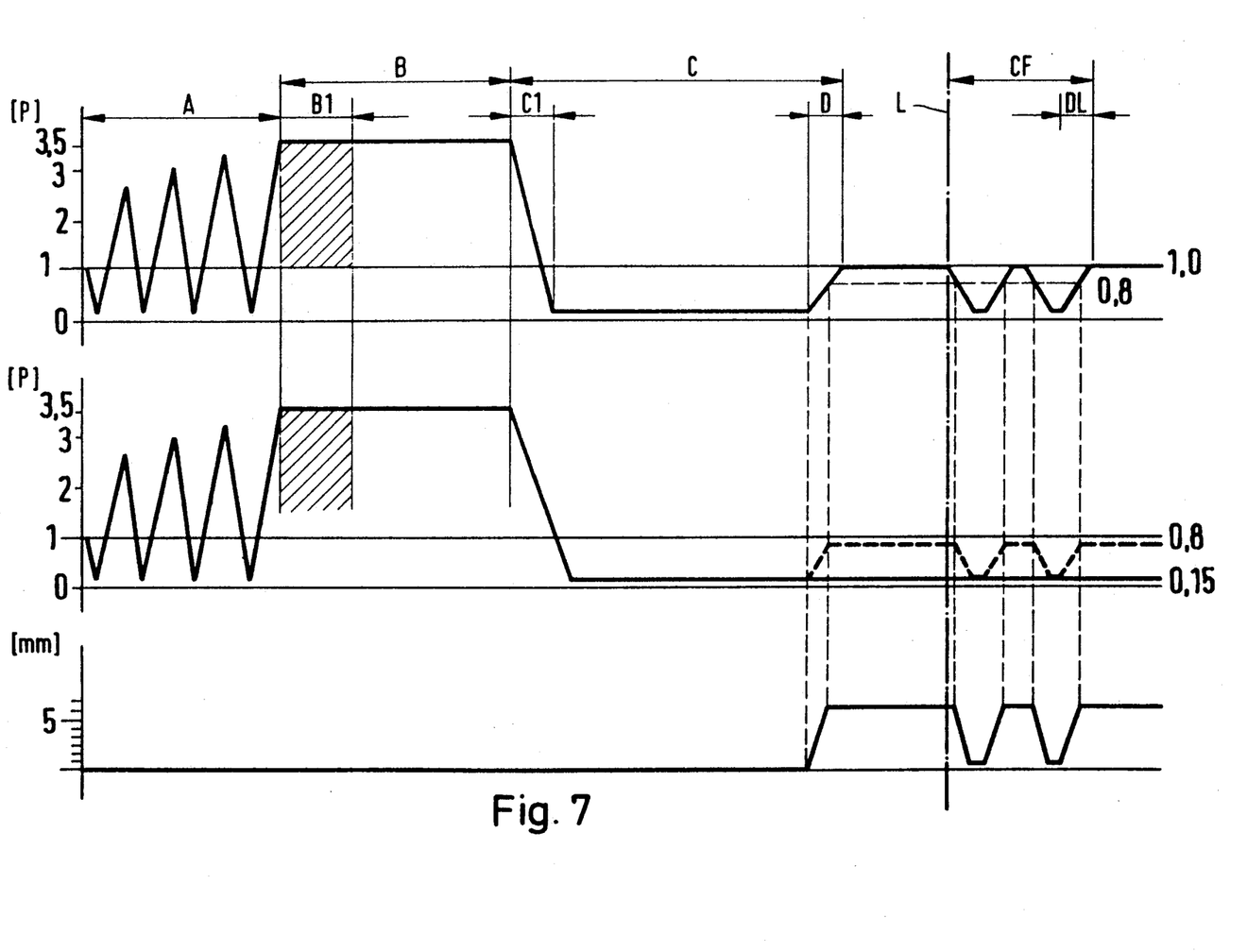
FIG. 7 is a graph showing the variation of pressure with time and the course of the movement with time.

In FIG. 7, the upper graph shows the pressure in the sterilizer chamber, the middle graph the pressure in the sensor (in solid line) and the pressure in the container (shown in dashed line starting from D) and the lower diagram shows the valve position.

Figure 8:
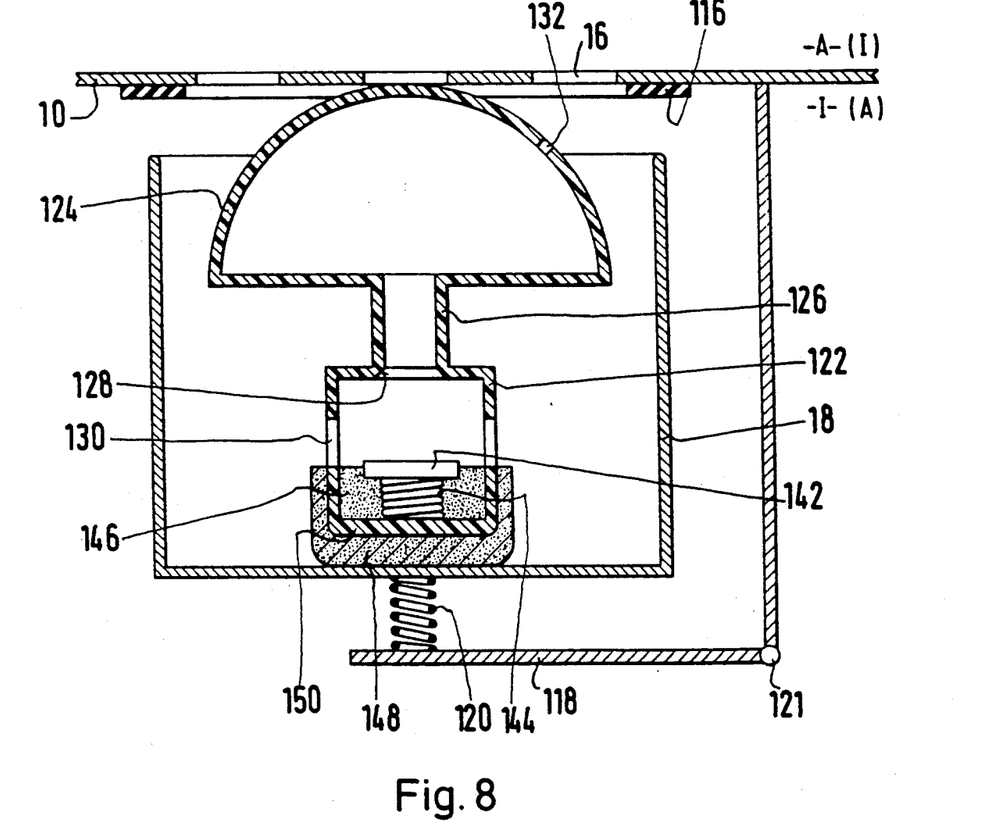
FIG. 8 is a diagrammatic view of another embodiment of a thermally controlled valve which is arranged in the lid of a sterilizer container.

FIG. 8 shows a section of the container lid 10 of a sterilizer container which is developed in known manner. The lid 10 is provided with fluid-exchange openings 16. The reference A designates the outside of the container and the reference I the inside of the container, i.e. the valve is arranged on the inside of the lid. However, it could also be arranged on the outside of the lid.

Around the fluid-exchange openings 16 a sealing ring 116 extends on the inside of the lid as valve seat against which a valve cap 18 can be pressed by a spring 120 which resets against a swing level 118. The swing level 118 can be locked in the position shown in the drawing and can be swung inward around its pivot axis 121.

In order to hold the valve open in the open position shown, a pressure capsule 124 of plastic is employed which, upon the application of a predetermined pressure difference, collapses into itself ("implodes") and thus opens the path for the closing of the valve under the action of the spring 120. This pressure capsule 124, which can only be used a single time, is of mushroom-shaped development and has a throttle opening 132 by which a delayed equalization of pressure can take place. The rod of the mushroom-shaped pressure capsule 124 which is in the form of a tubular extension 126 is in communication with a cage 122 which has lateral passage openings 130 and a valve seat 128 on the lower end of the tubular extension 126. A valve body 142 cooperates with the valve seat 128 and is under the action of a valve spring 144 which urges the valve body 142 into the closed position. The closing movement of the valve body 142 is, however, prevented by a thermal seal 146 which is adapted to the corresponding sterilization temperature and is cast in the lower cup-shaped part 150 of the gate 122 and keeps the valve body in the open position. This seal consists of a material which melts at a predetermined temperature then freeing the valve body so that it can close the capsule 124. In order to obtain a time delay in the closing movement and shift the closing of the valve, and thus the collapse of the pressure capsule 124, into the region of the ventilation phase, the lower cup-shaped part 150 is surrounded by an insulating body 148, also of cup shape, which permits the temperature to arrive with time delay at the thermal seal, which may consist of a plastic composition or an alloy.

The valve of the invention operates as follows:

In the pre-vacuum phase, a free exchange of fluid can take place via the passage openings 130, the raised valve body 18, and the fluid exchange openings 16. In this way, the pressure capsule 124 is retained in the shape shown in the drawing and rests, on top, against the lid 10 and, on bottom, via its insulating member 148 against the valve cap 14. In this way, the valve is held in open position against the action of the closing spring 120. This open position is retained also during the sterilization phase during which the sterilization chamber is exposed to increased pressure and increased temperature. This increased temperature produces, with time delay via the thermal insulating member 148, a gradual heating of the thermal seal 146. The transfer of heat through the insulating member and the cup-shaped part 150 as well as the softening or melting point of the thermal seal 146 are so adapted to each other that the auxiliary valve 62, 64, 128, 142 cannot be closed in the pre-vacuum phase A but only at the start B1 of the sterilization phase B. Pressure differences in the vacuum phase can be counteracted with time delay by the throttle opening 132. In the last vacuum phase therefore the internal pressure of the capsule 124 is identical to the surrounding pressure also when the valve 142, 128 is closed. In the ventilation phase, the increase in pressure takes place so rapidly that, despite the throttle opening 132, a considerable pressure difference can build up over the pressure capsule 124 so that this capsule collapses, i.e. implodes, as a result of a predetermined pressure difference acting upon it and in this way releases the valve cap 18 which is then pressed against the valve seat 116 by the spring 120 so that the container can now be sealed off while maintaining a predetermined vacuum in the sterilizer container.

The shaped of the valve shown in the drawing is merely intended to indicate its function. Structurally, numerous modifications are conceivable.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Apparatus for controlling the flow of fluid between a sterilizer container and a sterilizer, said sterilizer container being adapted to be disposed in the sterilizer, the sterilizer having a sterilization cycle, the cycle having a sterilization phase, a drying phase following the sterilization phase, and a ventilation phase following the drying phase, the sterilizer reaching a predetermined temperature during the sterilization phase and the pressure being reduced during the drying phase and thereafter being increased to a predetermined pressure during the ventilation phase, the apparatus comprising:

a valve cap disposed for movement on a sterilizer container between an open position and a closed position for exchanging fluid in the open position between the sterilizer container and a sterilizer during a sterilization phase, the valve cap closing off an aperture in the sterilizer container when in the closed position;

a temperature sensitive adjusting member disposed on the valve cap which enables the valve cap to close only after a predetermined temperature is reached;

a pressure sensitive member disposed on the valve cap, said pressure sensitive member having a chamber which communicates with the sterilizer via a first opening;

a biasing means for normally maintaining said valve cap in an open position when the pressure in said chamber of the pressure sensitive member and the sterilizer are substantially the same;

a second opening provided in said pressure sensitive member for allowing communication between the chamber and the sterilizer and which is closable by said temperature sensitive adjusting member when the predetermined temperature in the sterilization phase is reached, said chamber thereafter being evacuated via said first opening during a drying phase when the pressure is reduced, said chamber thereafter closing when the pressure in said sterilizer is increased to a predetermined pressure during a ventilation phase, causing said valve cap to move so as to close said aperture in the sterilizer container and seal the sterilizer container from the sterilizer at said predetermined pressure.

2. The apparatus recited in claim 1, wherein said first opening in said chamber of said pressure sensitive member comprises a one-way valve means for allowing pressure equalization from inside the chamber to outside the chamber, the chamber comprising means, compressed by a pressure difference between the inside and the outside upon reaching the predetermined pressure during the ventilation phase, for sealing the valve cap to the sterilizer container and closing communication through said aperture between the container and the sterilizer, with any increase in pressure outside the sterilizer container acting on the valve cap to maintain the valve cap in a closed condition.

3. The apparatus recited in claim 1, wherein said temperature-sensitive adjusting member comprises manually operable means for allowing manual opening of said second opening for equalizing pressure in said sterilizer and said chamber of said pressure-sensitive means, and further wherein said one-way valve means equalizes pressure in said chamber and said sterilizer container when said second opening is manually opened.

4. The apparatus recited in claim 3, wherein said temperature-sensitive adjusting member is pivotable around a pivot point and includes means for allowing the temperature sensitive adjusting member to be rotated in a first direction so as to maintain the second opening in an open position, but preventing movement in an opposite second direction to close the second opening unless the temperature in said sterilizer reaches said predetermined temperature.

5. The apparatus recited in claim 3, further comprising a replaeable filter provided in said one-way valve means.

6. The apparatus recited in claim 4, wherein the valve cap is supported in the open position by said chamber of said pressure sensitive means, the valve cap including a pot-shaped support body comprising resilient material maintained in an expanded condition by said biasing means, said biasing means comprising a spring, said chamber further comprising a hollow head piece disposed on the valve cap, said support body being in fluid communication with an interior of the hollow head piece, said second opening to the chamber being disposed on the head piece, and comprising a valve opening which can be blocked off by a plug of the temperature sensitive adjusting member movably disposed on the valve cap.

7. The apparatus recited in claim 6, wherein the temperature sensitive adjusting member is rotatably mounted on the valve cap and is urged into a position to close said second opening, said rotatable mounting of the temperature sensitive adjusting member allowing manual opening of said second opening, said temperature sensitive adjusting member comprising a temperature responsive member disposed thereon so that the adjusting member can move into a position to close the second opening when the temperature responsive member has reached the predetermined temperature.

8. The apparatus recited in claim 7, wherein the temperature sensitive adjusting member has an axis of rotation, the temperature responsive member having a drum coaxial to the pivot point, a sleeve extending into the drum, the temperature responsive member forming a coupling, the coupling having an alloy which melts at the predetermined temperature, the alloy being connected to the drum and the sleeve and fixing the drum and sleeve for rotation together when the alloy is in a solid state before reaching the predetermined temperature and allowing the drum and sleeve to rotate with respect to each other when in a molten state upon reaching the predetermined temperature.

9. The apparatus recited in claim 1, wherein the valve cap with the pressure sensitive member and temperature sensitive adjusting member includes means disposed thereon for removably fastening the valve cap on the sterilizer container.

10. The apparatus recited in claim 1, wherein the valve cap is arranged in a cup shaped depression of the sterilizer container, the depression having a bottom provided with said aperture, the valve cap being axially movable to seal said valve cap to the container and prevent communication between said container and sterilizer through said aperture.

* * * * *